United States Patent
Kim

(10) Patent No.: US 11,397,472 B1
(45) Date of Patent: Jul. 26, 2022

(54) ANTI-MOTION SICKNESS SYSTEMS AND METHODS

(71) Applicant: Ford Global Technologies, LLC, Dearborn, MI (US)

(72) Inventor: Roxanne Kim, Santa Clara, CA (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 17/204,114

(22) Filed: Mar. 17, 2021

(51) Int. Cl.
*G06F 3/01* (2006.01)
*B60R 11/04* (2006.01)
*G06T 7/30* (2017.01)

(52) U.S. Cl.
CPC .............. *G06F 3/017* (2013.01); *B60R 11/04* (2013.01); *G06F 3/011* (2013.01); *G06T 7/30* (2017.01); *G06T 2207/30201* (2013.01)

(58) Field of Classification Search
CPC .......... G06F 3/0481; G06F 3/011; G06T 7/30; G06T 2207/302; G60R 11/04
See application file for complete search history.

(56) References Cited

U.S. PATENT DOCUMENTS

| | | | | |
|---|---|---|---|---|
| 11,210,796 | B2* | 12/2021 | Feng | G06V 40/161 |
| 2006/0015000 | A1* | 1/2006 | Kim | A61M 21/02 |
| | | | | 600/27 |
| 2006/0079729 | A1* | 4/2006 | Kim | G16H 40/63 |
| | | | | 600/21 |
| 2007/0296820 | A1* | 12/2007 | Lonn | G06T 7/73 |
| | | | | 348/207.99 |
| 2008/0239104 | A1* | 10/2008 | Koh | H04N 5/23222 |
| | | | | 348/240.99 |
| 2018/0005495 | A1* | 1/2018 | Hieb | G08B 13/19682 |
| 2018/0184014 | A1* | 6/2018 | Goldstein | G06F 3/04817 |
| 2019/0047498 | A1* | 2/2019 | Alcaidinho | A61M 21/00 |
| 2019/0061655 | A1* | 2/2019 | Son | B60Q 3/70 |
| 2019/0133511 | A1 | 5/2019 | Migneco et al. | |
| 2020/0061332 | A1 | 2/2020 | Dry et al. | |

OTHER PUBLICATIONS

Alexander Meschtscherjakov et al, "Bubble Margin: Motion Sickness Prevention While Reading on Smartphones in Vehicles", Center for Human-Computer Interaction, University of Salzburg, Salzburg, Austria, published by Springer Nature Switzerland AG, Interact 2019, LNCS 11747, 2019, 18 pages.

* cited by examiner

*Primary Examiner* — Haoshian Shih
(74) *Attorney, Agent, or Firm* — Brandon Hicks; Eversheds Sutherland (US) LLP

(57) ABSTRACT

Anti-motion sickness systems and methods are disclosed herein. An example method can include determining alignment of a face of a user with an alignment tool provided on a display of a user device. When the face is aligned with the alignment tool the user device is in a preferred orientation. Providing a camera feed on the display, and determining a current orientation of the user device. The method can include presenting selected content on the display in combination with the camera feed. A location of the selected content on the display can be based on the current orientation of the user device. The selected content can be centered on the display when the current orientation substantially matches the preferred orientation.

20 Claims, 7 Drawing Sheets

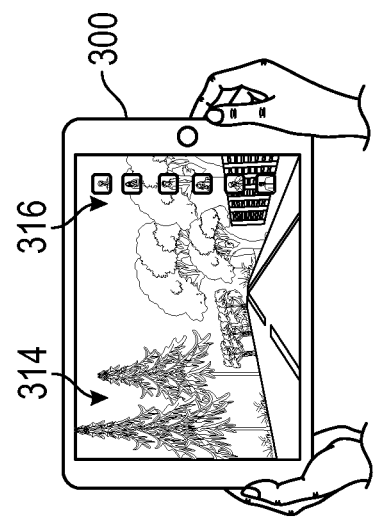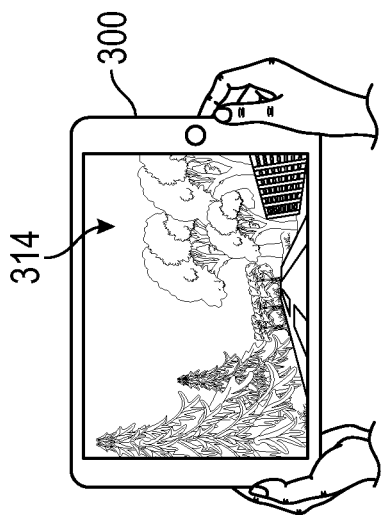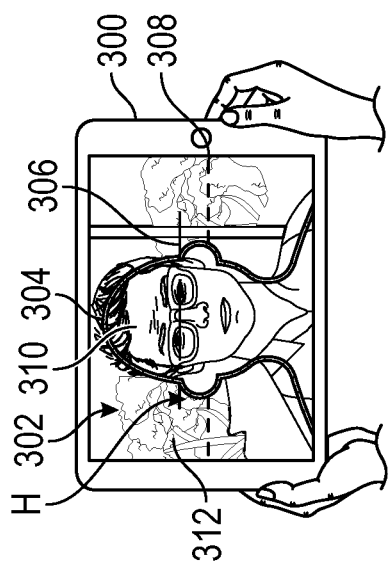
FIG. 3A FIG. 3B FIG. 3C

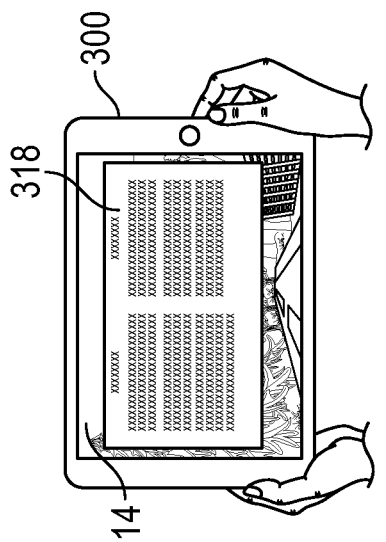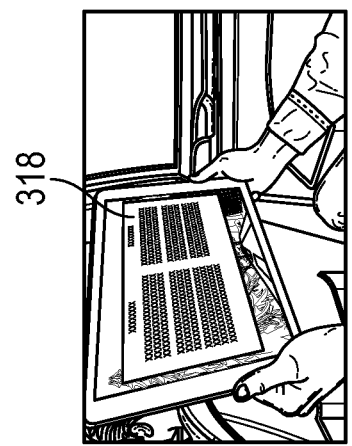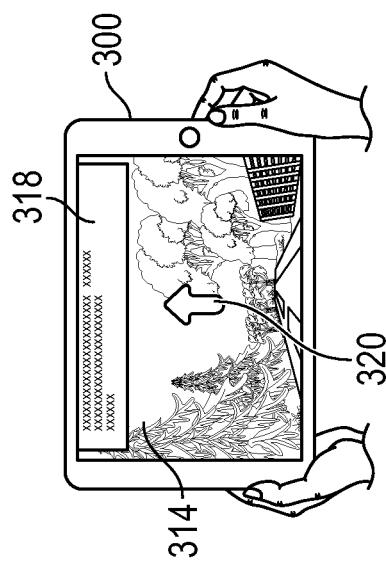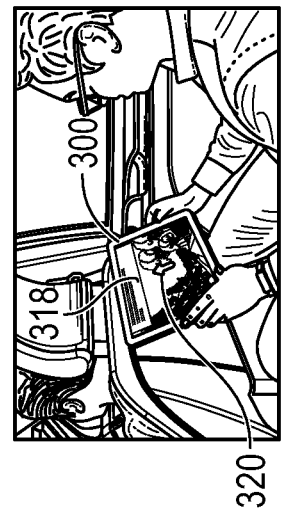
FIG. 3E
FIG. 3D

ANTI-MOTION SICKNESS SYSTEMS AND METHODS

BACKGROUND

It is common for passengers in a vehicle to experience motion sickness, particularly passengers in seats that are not in the front of the vehicle, such as those in the second or third row. It is also common for passengers to experience motion sickness when they try to read books, email on their phones, and/or try and watch movies on their devices. Human motion sickness can be influenced by a complex interaction of body senses, including the ears, eyes, and nervous system. Those who experience motion sickness do so because they may receive conflicting messages from these body systems.

In one example, a passenger seated in the rear seat of a vehicle has a limited view, with a headrest between them and the view out of the front window. When the vehicle is moving, even though the passenger's ears and body experience the motion, their eyes provide them with conflicting information, and they may experience motion sickness. On the contrary, the driver, who has a view of the road he is traveling on, and whose body experiences motion that correlates with that view, does not typically experience motion sickness.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

FIGS. 3A-3E collectively illustrate an example process for aligning a user device using an Anti-Motion Sickness Application and allowing a user to view selected content.

DETAILED DESCRIPTION

Overview

The present disclosure is directed to systems and methods for reducing motion sickness for vehicle occupants while the occupants are performing a task, such as reading a book. The system may include an Anti-Motion Sickness Application (AMSA) for a user's personal device. This AMSA may enable the position and orientation of their personal device to be determined, and may also enable the front view cameras of the vehicle to be displayed on the personal device.

In some instance, the application may function as follows. First, the user opens the Anti-Motion Sickness Application (AMSA) and matches his eye level by using the front camera of the user device in order to be "looking forwards." Second, the camera feed from the front view camera of the vehicle is fed to the personal device, and the user selects a second application to open (for example a reading application). Third, once the second application is selected, the AMSA may provide an indication on the screen of the personal device for the user to move the personal device in the direction in which the user would be looking forward. This may be determined using sensors of the phone and an arrow that may indicate the direction the device should be is substantially orthogonal to the road. Fourth, as the user moves their personal device in the direction indicated, eventually the second application will come into view on the personal device. The workspace/second application area is essentially floating, and is not captured onto the screen of the personal device until the device is positioned and orientated to be in an acceptable location.

Figure 1:
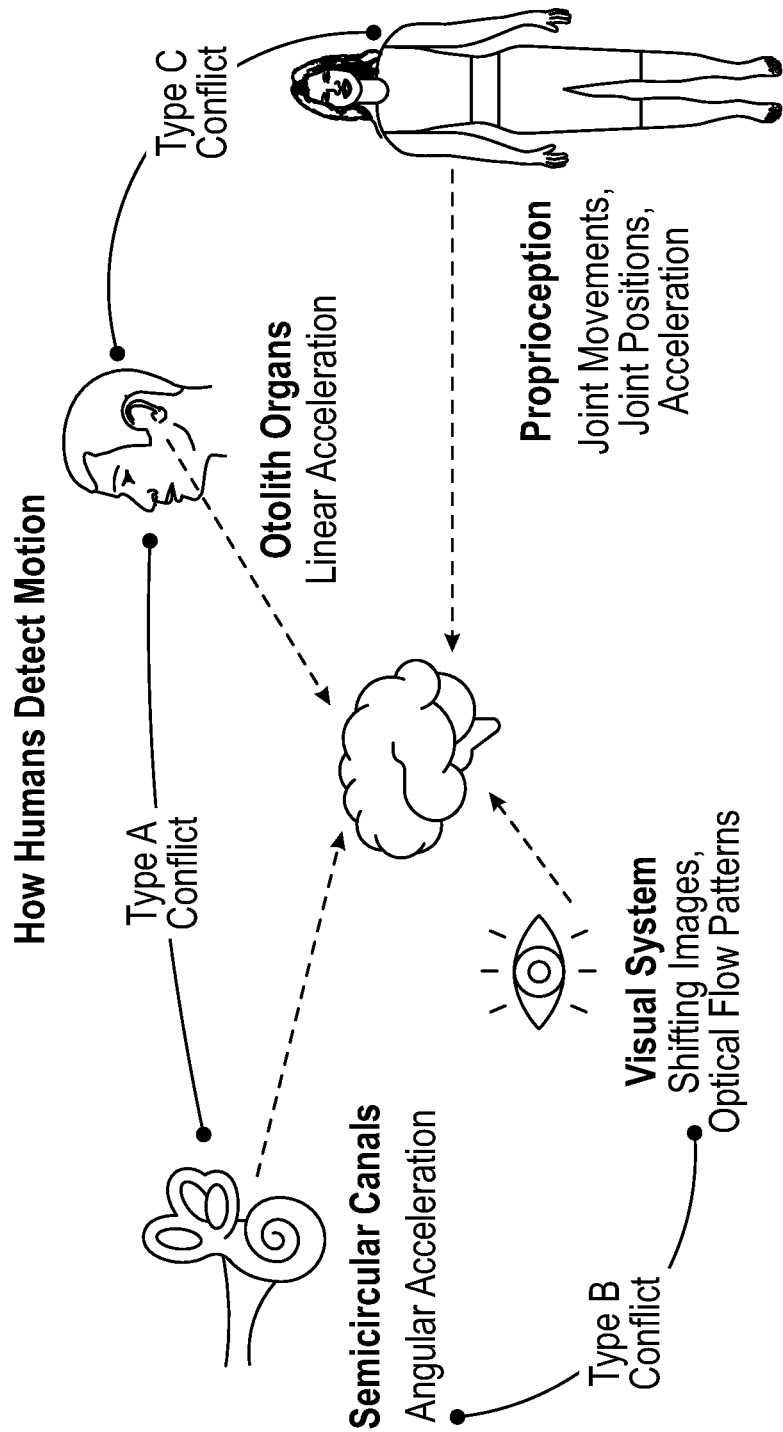
FIG. 1 is a prior art diagram of example causes of motion sickness in humans.

FIG. 1 is a prior art depiction of how a human can detect motion. Motion can be detected through physical systems semi-circular ear canals, otolith organs, proprioception, and visual systems. Conflicts can be realized between each of these physical systems. To reduce or minimize the chances of experiencing motion sickness, the individual may desire to reduce or eliminate these conflicting messages. FIG. 1 also illustrates example conflict types A and B. Conflict type C involves conflicts between otolith organs and proprioception.

ILLUSTRATIVE EMBODIMENTS

Figure 2:
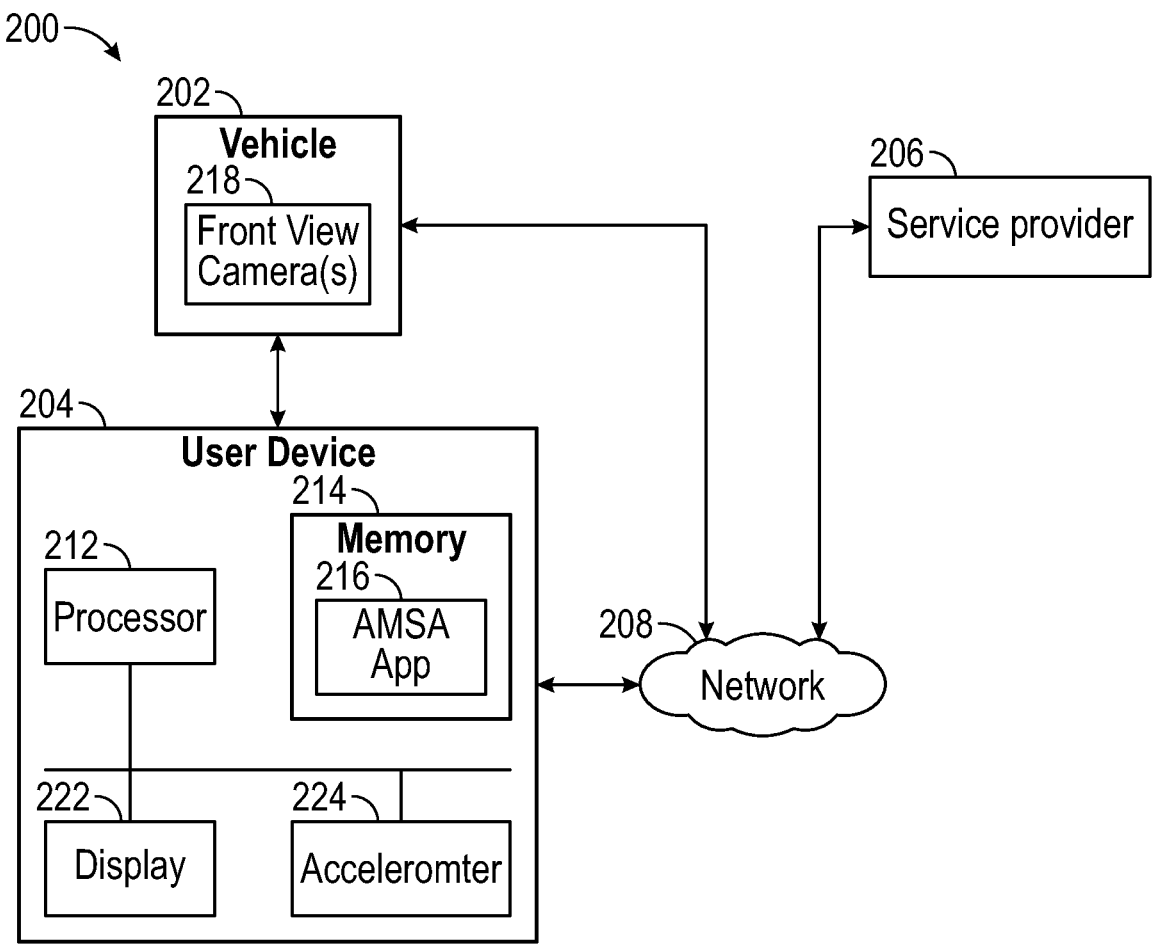
FIG. 2 depicts an illustrative architecture in which techniques and structures for providing the systems and methods disclosed herein may be implemented.
Figure 2:
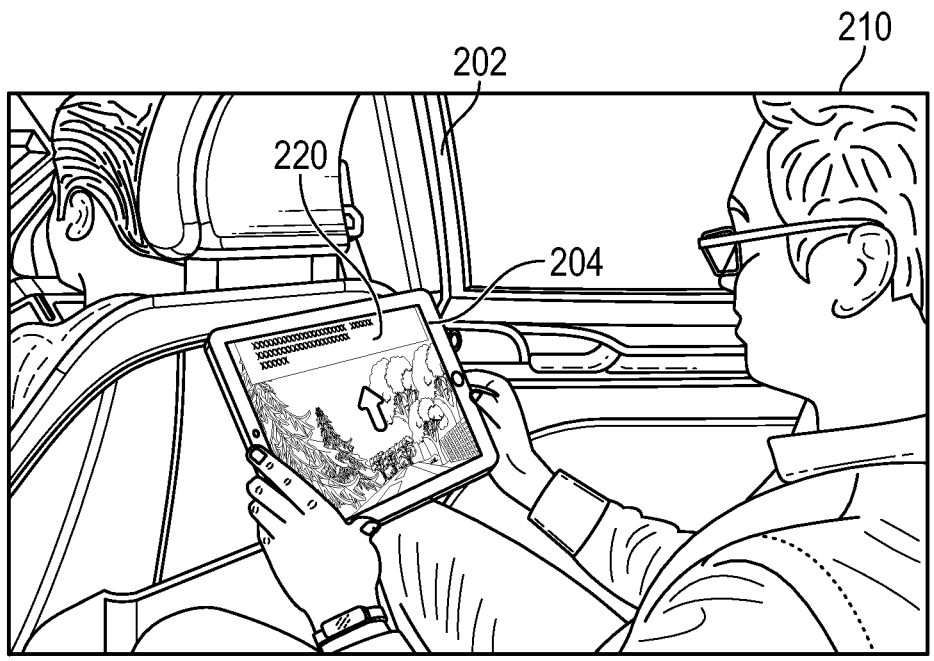

Turning now to the drawings, FIG. 2 depicts an illustrative architecture 200 in which techniques and structures of the present disclosure may be implemented. The architecture 200 can include a vehicle 202, a user device 204, a service provider 206, and a network 208. Some or all of these components in the architecture 200 can communicate with one another using the network 208. The network 208 can include combinations of networks that enable the components in the architecture 200 to communicate with one another. The network 208 may include any one or a combination of multiple different types of networks, such as cable networks, the Internet, wireless networks, and other private and/or public networks. In some instances, the network 208 may include cellular, Wi-Fi, or Wi-Fi direct.

A user 210 controls the user device 204 while traveling in the vehicle 202. The user device 204 can comprise a processor 212 and memory 214. The processor 212 executes instructions stored in memory 214 to perform any of the anti-motion sickness features disclosed herein. In one example, the instructions can include an application, referred to as an anti-motion sickness application (AMSA application 216). The user device can also include a display 222 and accelerometer 224.

The user 210 can download the AMSA application 216 onto the user device 204. The AMSA application 216 may determine a position and an orientation of the user device 204. The AMSA application 216 may enable a camera feed from front-view cameras 218 of the vehicle 202 to be displayed on the user device 204. When the user 210 may desire to view desired content 220 on their user device 204 such as an e-book, a social media application, a video, and so forth. Prior to viewing their desired content 220, the user 210 may launch the AMSA application 216 or in tandem with their selected content. The concurrent execution of the AMSA application 216 with the content 220 reduces the likelihood that the user may experience motion sickness. To be sure, rather than requiring the user 210 to launch the AMSA application 216, the AMSA application 216 the processor 212 can be configured to launch the AMSA application 216 when the processor 212 determines that the user device 204 is moving at or above a specified rate of speed. For example, the processor 212 can determine that the accelerometer 224 of the user device 204 has detected that the user device 204 is moving at a rate of speed that exceeds ten miles per hour. It will be understood that other rate of speed values can be used. In general, the AMSA application 216 can obtain a camera feed from the front-view cameras 218 and present the same on the display 222 of the user device 204.

In some configurations, the AMSA application 216 can communicate with the service provider 206. For example, the service provider 206 can determine if the AMSA application 216 is connected with the front-view cameras 218 and obtaining a camera feed. Additional details regarding these features are disclosed in greater detail infra. In one example, the user device 204 can be connected to the front-facing cameras 218 over a short-range wireless connection or over a wired connection available in the vehicle 202. In another example, when the vehicle 202 is a connected vehicle that transmits a camera feed of the front-facing cameras 218 to the service provider 206, the AMSA application 216 can obtain the camera feed from the service provider 206. Thus, the AMSA application 216 can obtain the camera feed directly from the vehicle 202 or the service provider 206.

FIGS. 3A-3E collectively illustrate an example process for executing an AMSA application on a user device, such as a tablet or Smartphone. The user device could include a display or workstation integrated into the vehicle. In FIG. 3A, can execute an AMSA application on their user device 300. The AMSA application generates and displays an alignment tool in the form of a user interface 302 that includes an outline 304 of a head with one or more reference lines. For example, a reference line 306 can be a line that may be displayed on the screen of the user device 300.

A front-facing camera 308 of the user device 300 can obtain images of a face 310 of a user. The images of the face 310 can be displayed on the screen of the user device 300. The user can move their body and/or the user device 300 to align their eyes along the reference line 306. In some instances, the alignment user interface 302 can include a horizon line 312 that may align with a natural horizon H. The user can be prompted to orient the user device 300 such that the horizon line 312 roughly or approximately aligns with the natural horizon H to ensure that the user is looking forward for alignment purposes. Also, placing the user in a forward-facing direction can reduce motion sickness. Once the horizon line 312 aligns with the natural horizon H and the eyes of the user is aligned with the reference line 306, the processor (see processor 212 of FIG. 2) of the user device 300 can establish this orientation as the preferred orientation. The orientation is determined based on the output of an accelerometer of the user device 300. As disclosed herein, movement of the user device away from this preferred orientation can result in motion sickness. Thus, processes for realigning the user device with the preferred orientation are disclosed infra.

Once alignment is complete where the user's face has been aligned with the alignment user interface 302, the AMSA application can obtain camera feed 314 from a camera of the vehicle and use the camera feed as a background of the user device 300 as illustrated in each of FIGS. 3B-3E. That is, the camera feed 314 may become the base or background displayed on the user device 300. The camera feed includes real-time video obtained as the vehicle is operated.

In FIG. 3C, the AMSA application display icons 316 that correspond to executable applications or content available to the user. These icons can be overlayed on top of the camera feed 314. In FIG. 3D, selected, desired content 318 can be displayed along with the camera feed 314. In this example, the desired content 318 can include a webpage or e-book.

Once the user has opened the AMSA application, the AMSA application may not allow the desired content 318 to be entirely viewable as illustrated in FIG. 3D. For example, the user has moved the user device 300 downwardly towards their lap. The AMSA application may provide an indication or guide 320 (such as an arrow) on the display. The indication or guide 320 may direct the user to move the user device 300 in a direction that ensures that the user is looking forward.

As noted above, the AMSA application can execute an algorithm that may determine an orientation of the user device 300 from an accelerometer within the user device 300 and/or an axis-based motion-sensing system. The AMSA application can use this orientation information to select where the indication or guide 320 may be displayed on the user device 300. The indication or guide 320 indicates a direction along which the device may be moved to enable the user device 300 to be substantially orthogonal to the road (e.g., aligned with the horizon H).

FIG. 3E illustrates the view of the display of the user device 300 after the user has moved the user device as indicated by the indication or guide 320. As the user moves their user device in the direction indicated, eventually the desired content 318 may come into view. The desired content 318 may essentially float on the display, and may not be centered onto the display of the user device until the user device has been positioned and oriented to be in an acceptable orientation (e.g., where the user is substantially forward-facing). Thus, the position/orientation of the user device is higher in FIG. 3E compared to FIG. 3D. In FIG. 3E, when the desired content 318 is in approximately full view, the user can read the e-book. As illustrated, the background remains the camera feed 314 obtained from the front view cameras of the vehicle. Thus, the user can see a view of the road ahead from the camera feed 314. The user has also been influenced to look in the direction of motion, and therefore the motion felt by their body may now be synchronized with the motion the user is currently experiencing. Collectively, these functionalities may reduce or eliminate the motion sickness experienced.

Figure 4:
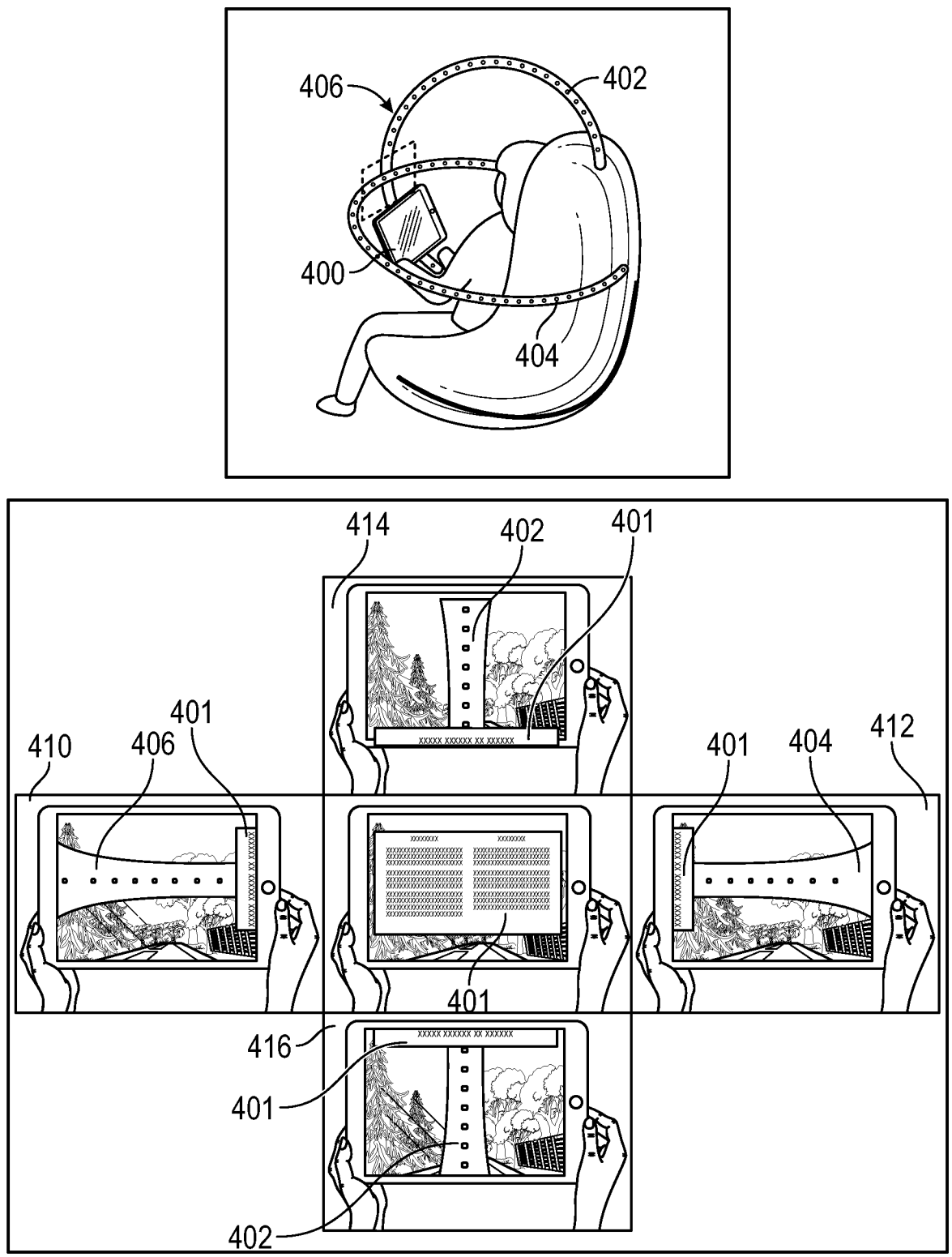
FIG. 4 illustrates an example user device orientation tracking and alignment process.

FIG. 4 illustrates real-time user device tracking and alignment. In this example, the AMSA application has been launched and is displaying the camera feed on the user device 400. An alignment frame having a vertical axis 402 and a horizontal axis 404 are established relative to an approximate preferred position 406 (e.g., preferred orientation) where the user is facing forward and their face is aligned with a natural horizon, as disclosed above. In some instances, the vertical axis 402 and the horizontal axis 404 intersect at the approximate preferred position 406.

Selected content 401 may be displayed on the user device 400 along with the camera feed. When the user device 400 is in the approximate preferred position 406, selected content 401 is positioned centrally on the display of the user device 400. That is, the user can view all or most of the selected content 401 when the user device is aligned with the alignment frame. When the user device 400 has been turned leftward 410 of the approximate preferred position 406, a portion of the horizontal axis 404 can be seen, along with a portion of the selected content 401 which can be viewed on a rightmost section of the user device 400. When the user device 400 has been turned rightward 412 of the approximate preferred position 406, a portion of the horizontal axis 404 can be seen, along with a portion of the selected content 401 which can be viewed on a leftmost section of the user device 400.

When the user device 400 has been turned upward 414 of the approximate preferred position 406, a portion of the vertical axis 402 can be seen, along with a portion of the selected content 401 which can be viewed on a lowermost section of the user device 400. When the user device 400 has been turned downward 416 of the approximate preferred position 406, a portion of the vertical axis 402 can be seen, along with a portion of the selected content 401 which can be viewed on an uppermost section of the user device 400.

In sum, as the user continues to view the selected content 401, the AMSA application continues to influence the user to keep his/her user device held in a correct orientation, such that the user is looking in the forward direction, his/her direction of travel, and has a view of the road ahead, minimizing motion sickness.

Figure 5:
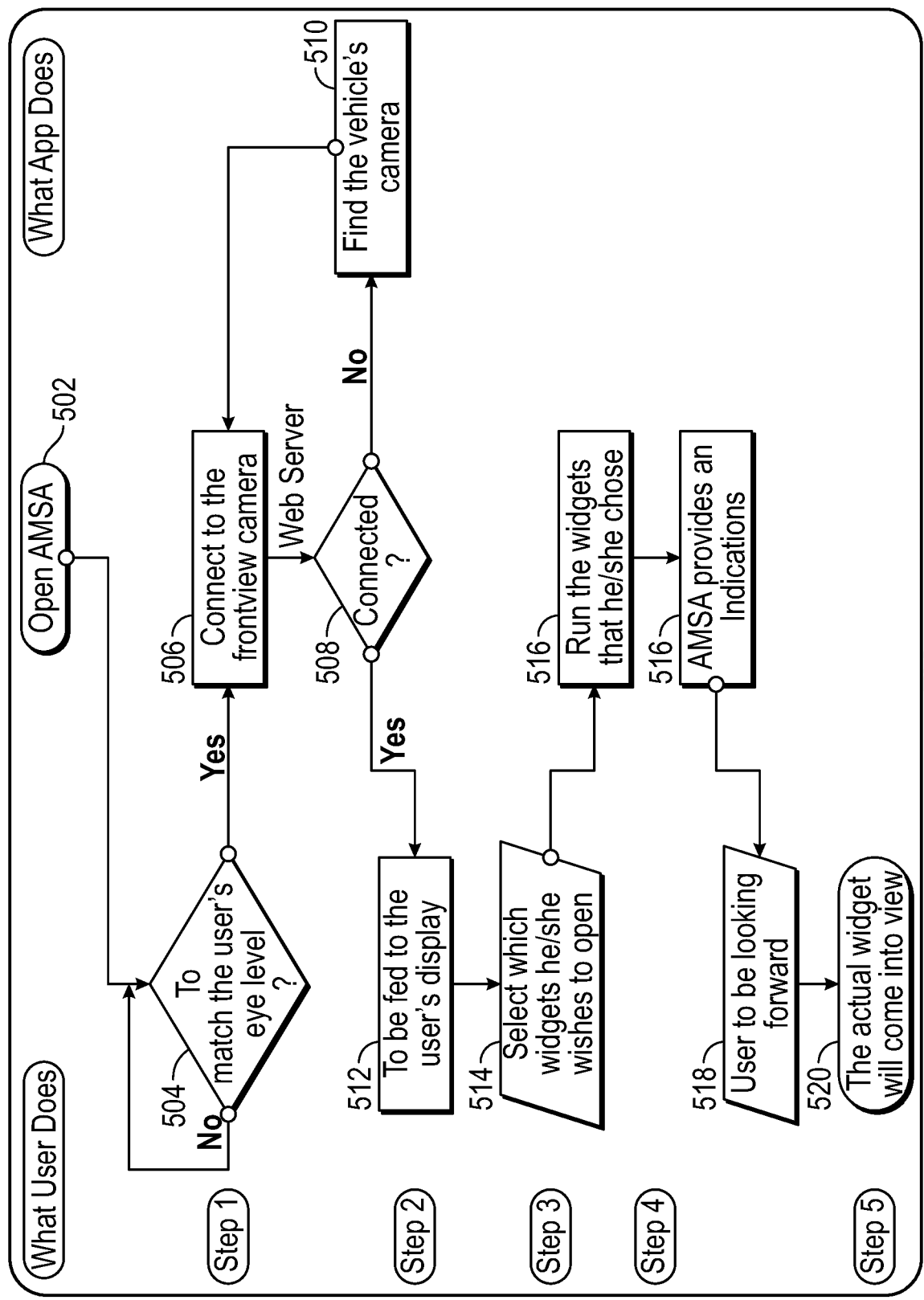
FIG. 5 is a flowchart of an example method of the present disclosure.

FIG. 5 is a flowchart of an example method of the present disclosure. The method includes a step 502 of executing an AMSA application on a user device. As noted above, a user can launch the AMSA application manually. Alternatively, the AMSA application can be launched automatically in response to certain criteria or movement thresholds related to the user device such as a rate of speed. In another example, the AMSA application can be triggered when the user device enters a mode of operation that indicates that the user device is being used in a vehicle, such as a car-play mode.

The method can include a step 504 of aligning a user's face with an alignment tool. For example, the user can match their eye position to an alignment line of the alignment tool. As noted above, a camera of the user device captures a feed of the user and displays the user's face on the display of the user device, along with the alignment tool. Once aligned, the method can include a step 506 of connecting to a camera feed of a vehicle camera. Step 508 includes determining when the AMSA application is connected to the camera feed. In one example, the AMSA application is communicatively coupled to a service provider. The service provider can determine if a connection to a camera feed has been achieved.

If the AMSA application is not connected, step 510 includes finding or detecting the vehicle camera. As noted above, this step can involve a service provider that can confirm when the camera feed is available. The method can include a step 512 of providing the camera feed to the display of the user device, along with a step 514 of determining one or more types of selected/desired content or application selected by a user of the user device. The method can include a step 516 of providing the desired content or application on the display of the user device. When the user has moved the user device from being in approximate preferred alignment (front-facing and level with the horizon), the method includes a step 518 of the AMSA application displaying an indication on the display of the user device. For example, the AMSA application may display an arrow or other alignment feature that directs the user to move the user device in a particular direction.

The method can include a step 520 of determining that the user device is in alignment with a preferred alignment for the user device as established by the AMSA application (e.g., using an alignment tool as disclosed above). When the user device is correctly oriented, the selected content or application (e.g., widget) may come into full view on the display of the user device.

In sum, the AMSA application provides an augmented reality experience where a camera feed is combined with selected content for display on a user device. The extent to which the selected content is viewable on the display is correlated to how aligned the user device is with an alignment frame or tool that is established by the AMSA application. Again, this alignment frame may be oriented so that that the user may be forward-facing relative to a direction of travel of a vehicle, and an eye line of the user may be substantially aligned with a natural horizon.

Figure 6:
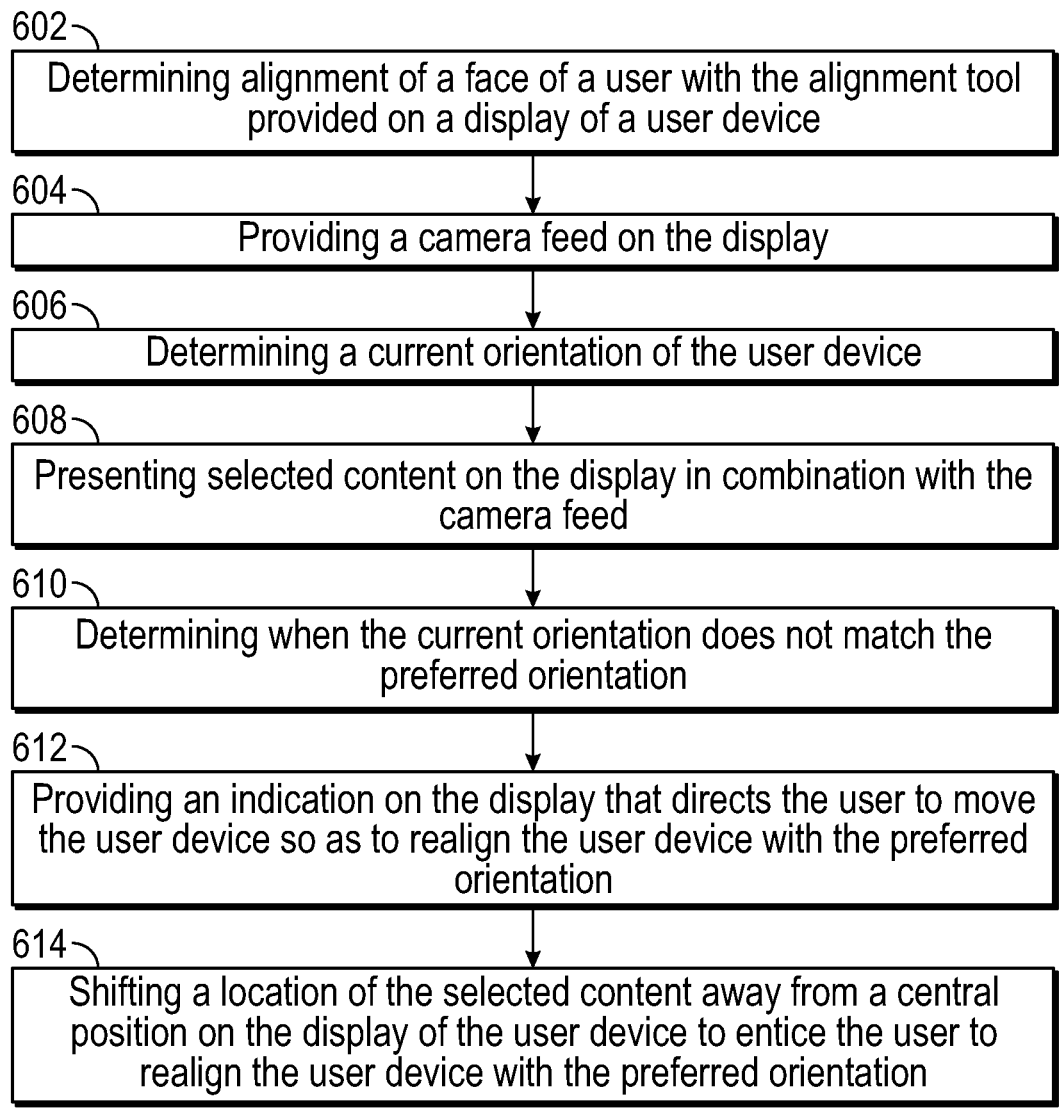
FIG. 6 is a flowchart of another example method of the present disclosure.

FIG. 6 is a flowchart of another example method. This method assumes that an AMSA application is functioning on a user device and a camera feed may be available to the user device. An alignment tool (see FIG. 3A as an example) can be presented on a display of the user device.

The method can include a step 602 of determining the alignment of a face of a user with the alignment tool provided on a display of a user device. The alignment tool can include a head outline, a reference line, and a horizon line. The user may align their head with the head outline, their eyes with the reference line, and a natural horizon with the horizon line.

The user device can be determined to be in a preferred orientation when the face of the user may be substantially aligned with the alignment tool. In some instances, the alignment need not be exact. The degree to which the alignment can differ can be established during the design of the AMSA application. Also, the preferred orientation can include aligning the eyes of the user with an eye reference line, as well as aligning a horizon reference line with a natural horizon.

The method can include a step 604 of providing a camera feed on the display, as well as a step 606 of determining a current orientation of the user device. The provision of the camera feed can include the user device receiving the camera feed directly from the vehicle/camera or a service provider. The current orientation can be determined using the output of an accelerometer of the user device. The current orientation can be compared against the preferred orientation of the user device that has been previously established using the alignment process above.

Next, the method can include a step 608 of presenting selected content on the display in combination with the camera feed. It will be understood that a location of the selected content on the display may be based on the current orientation of the user device. In some instances, the selected content can be centered on the display when the current orientation substantially matches the preferred orientation.

The method can further include a step 610 of determining when the current orientation does not match the preferred orientation. As noted above, the preferred orientation may be established and stored by the user device. The preferred orientation can be determined from output from an accelerometer in some instances. This preferred orientation can be considered a baseline orientation.

The method can include a step 612 of providing an indication on the display that directs the user to move the user device so as to realign the user device with the preferred orientation. This indication can be displayed when the current orientation does not correspond to (e.g., match) the preferred orientation. That is, the current output from the accelerometer of the user device can be compared to the baseline accelerometer output of the preferred orientation. When a deviation between these orientations is determined, the indication can be displayed. Also, the method can include a step 614 of shifting a location of the selected content away from a central position on the display of the user device. This shifting action places the selected content in a less-than-optimal viewing location to entice the user into realigning a current orientation of the user device with the preferred orientation. In sum, the AMSA application can provide the user with instructions or indications that direct the user to realign the user device with the preferred orientation to reduce a likelihood that the user will experience motion sickness when using the user device in a moving vehicle.

Implementations of the systems, apparatuses, devices, and methods disclosed herein may comprise or utilize a special purpose or general-purpose computer including computer hardware, such as, for example, one or more processors and system memory, as discussed herein. Computer-executable instructions comprise, for example, instructions and data which, when executed at a processor, cause a general-purpose computer, special purpose computer, or special purpose processing device to perform a certain function or group of functions. An implementation of the devices, systems, and methods disclosed herein may communicate over a computer network. A "network" is defined as one or more data links that enable the transport of electronic data between computer systems and/or modules and/or other electronic devices.

Further, it should be noted that any or all of the aforementioned alternate implementations may be used in any combination desired to form additional hybrid implementations of the present disclosure. For example, any of the functionality described with respect to a particular device or component may be performed by another device or component. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching.

What is claimed is:

1. A method comprising:
   determining a current orientation of a user device;
   directing a user to position the user device in a preferred orientation using an alignment tool on a display of the user device;
   providing a camera feed on the display; and
   presenting selected content on the display in combination with the camera feed, wherein a location of the selected content on the display is based on the current orientation of the user device, and wherein the selected content is centered on the display when the current orientation substantially matches the preferred orientation.

2. The method according to claim 1, further comprising displaying the alignment tool, the alignment tool comprising a head outline, a reference line, and a horizon line, wherein the user aligns a head of the user with the head outline, eyes of the user with the reference line, and a natural horizon with the horizon line.

3. The method according to claim 1, further comprising determining when the camera feed is available.

4. The method according to claim 1, wherein the camera feed is displayed as a background on the display and the selected content is displayed on top of the camera feed.

5. The method according to claim 1, further comprising:
   determining when the current orientation does not match the preferred orientation; and
   providing an indication on the display that directs the user to move the user device so as to realign the user device with the preferred orientation.

6. The method according to claim 5, further comprising:
   determining when the current orientation does not match the preferred orientation; and
   selectively altering the location of the selected content on the display to entice the user to realign the user device with the preferred orientation.

7. The method according to claim 6, wherein the current orientation is determined from output of an accelerometer of the user device.

8. The method according to claim 1, further comprising obtaining the camera feed from a vehicle, the user device being present within the vehicle.

9. A user device comprising:
   a display, an accelerometer, a processor, and a memory for storing instructions, the processor executing instructions stored in the memory to:
      present an alignment tool on the display, wherein the alignment tool is configured to allow a user to align their face with a head outline and a natural horizon with a horizon line to place the user device in a preferred orientation;
      provide a camera feed on the display;
      provide selected content in combination with the display;
      determine when the user has moved the user device away from the preferred orientation; and
      instruct the user to realign the user device with the preferred orientation.

10. The user device according to claim 9, wherein the instructions comprise an application, the processor being configured to launch the application when the user device is moving at a rate of speed that exceeds a threshold based on output of the accelerometer.

11. The user device according to claim 9, wherein the camera feed is obtained from a forward-facing camera of a moving vehicle.

12. The user device according to claim 9, wherein the alignment tool comprises a reference line, wherein the user aligns their eyes with the reference line.

13. The user device according to claim 9, wherein the processor is configured to determine when the camera feed is available.

14. The user device according to claim 9, wherein the processor is configured to display the camera feed as a background on the display and the selected content on top of the camera feed.

15. The user device according to claim 9, wherein the processor is configured to:
   determine when a current orientation of the user device does not match the preferred orientation; and
   provide an indication on the display that directs the user to move the user device so as to realign the user device with the preferred orientation.

16. The user device according to claim 15, wherein the processor is configured to:
   determine when the current orientation does not match the preferred orientation, the current orientation being determined from output of the accelerometer of the user device; and
   alter a location of the selected content on the display to entice the user to realign the user device with the preferred orientation.

17. A system comprising:
   a camera;
   a user device comprising a display; and
   a processor and a memory for storing instructions, the processor executing instructions stored in the memory to:
      determine a current orientation of the user device;
      direct a user to position the user device in a preferred orientation using an alignment tool on the display of the user device;
      provide a camera feed on the display; and
      present selected content on the display in combination with the camera feed, wherein a location of the selected content on the display is based on the current orientation of the user device, and wherein the selected content is centered on the display when the current orientation substantially matches the preferred orientation.

18. The system according to claim 17, wherein the processor is configured to display the alignment tool, the alignment tool comprising a head outline, a reference line, and a horizon line, wherein the user aligns a head of the user with the head outline, eyes of the user with the reference line, and a natural horizon with the horizon line.

19. The system according to claim 17, wherein the processor is configured to determine when the camera feed is available.

20. The system according to claim 19, wherein the camera feed is displayed as a background on the display and the selected content is displayed on top of the camera feed.

* * * * *